United States Patent
Gokaraju et al.

(10) Patent No.: US 11,576,941 B2
(45) Date of Patent: Feb. 14, 2023

(54) TASTE MASKING FORMULATION FOR BITTER NATURAL COMPOUNDS

(71) Applicant: LAILA NUTRACEUTICALS, Vijayawada (IN)

(72) Inventors: Ganga Raju Gokaraju, Vijaywada (IN); Rama Raju Gokaraju, Vijayawada (IN); Kishore Babu Govada, Vijayawada (IN); Venkata Krishna Raju Alluri, Vijayawada (IN); Nagendra Babu Vutti, Vijayawada (IN); Kiran Bhupathiraju, Vijayawada (IN); Venkata Kanaka Ranga Raju Gokaraju, Vijayawada (IN); Trimurtulu Golakoti, Vijayawada (IN)

(73) Assignee: LAILA NUTRACEUTICALS, Vijayawada (IN)

( * ) Notice: Subject to any disclaimer, the term of this patent is extended or adjusted under 35 U.S.C. 154(b) by 0 days.

(21) Appl. No.: 16/312,150

(22) PCT Filed: Jun. 21, 2017

(86) PCT No.: PCT/IN2017/050251
§ 371 (c)(1),
(2) Date: Dec. 20, 2018

(87) PCT Pub. No.: WO2017/221268
PCT Pub. Date: Dec. 28, 2017

(65) Prior Publication Data
US 2019/0201470 A1 Jul. 4, 2019

(30) Foreign Application Priority Data
Jun. 21, 2016 (IN) .............................. 201641021154

(51) Int. Cl.
| | |
|---|---|
| A61K 36/68 | (2006.01) |
| A23L 33/105 | (2016.01) |
| A23L 27/00 | (2016.01) |
| A61K 9/16 | (2006.01) |
| A61K 31/7048 | (2006.01) |
| A61K 47/32 | (2006.01) |
| A61K 47/36 | (2006.01) |
| A61K 47/44 | (2017.01) |
| A61K 36/19 | (2006.01) |
| A61K 36/22 | (2006.01) |
| A61K 36/324 | (2006.01) |
| A61K 36/38 | (2006.01) |
| A61K 36/42 | (2006.01) |
| A61K 36/58 | (2006.01) |
| A61K 36/81 | (2006.01) |

(52) U.S. Cl.
CPC .............. *A61K 36/68* (2013.01); *A23L 27/84* (2016.08); *A23L 33/105* (2016.08); *A61K 9/1635* (2013.01); *A61K 31/7048* (2013.01); *A61K 47/32* (2013.01); *A61K 47/36* (2013.01); *A61K 47/44* (2013.01); *A23V 2002/00* (2013.01); *A23V 2200/16* (2013.01); *A23V 2300/31* (2013.01); *A23V 2300/40* (2013.01); *A61K 36/19* (2013.01); *A61K 36/22* (2013.01); *A61K 36/324* (2013.01); *A61K 36/38* (2013.01); *A61K 36/42* (2013.01); *A61K 36/58* (2013.01); *A61K 36/81* (2013.01)

(58) Field of Classification Search
None
See application file for complete search history.

(56) References Cited

U.S. PATENT DOCUMENTS

| | | | | |
|---|---|---|---|---|
| 6,153,220 A | * | 11/2000 | Cumming | A61P 25/20 424/464 |
| 2011/0212171 A1 | | 9/2011 | Venkatesh et al. | |
| 2012/0276199 A1 | | 11/2012 | Bondu et al. | |

FOREIGN PATENT DOCUMENTS

| | | | | |
|---|---|---|---|---|
| WO | WO 02/43707 A1 | 6/2002 | | |
| WO | WO 2004/087111 A1 | 10/2004 | | |
| WO | WO 2005/055987 A1 | 6/2005 | | |
| WO | WO-2007093897 A2 | * | 8/2007 | ............. A61K 36/59 |
| WO | WO 2008/107296 A1 | 9/2008 | | |
| WO | WO 2015/091068 A1 | 6/2015 | | |

OTHER PUBLICATIONS

Written Opinion of the International Searching Authority and International Search Report dated Nov. 7, 2017 for PCT/IN2017/050251.

* cited by examiner

*Primary Examiner* — Russell G Fiebig
(74) *Attorney, Agent, or Firm* — Kramer & Amado, P.C.

(57) ABSTRACT

The invention discloses taste masking formulations for bitter natural compounds, selected from the extracts, fraction and pure phytochemicals produced in combination with a synthetic polymer or a natural polymer. The invention also relates to the novel process of producing the taste masking formulations. The invention also relates to taste masking formulations of *Bacopa* extracts with no bitter taste or negligible bitter taste in combination with synthetic polymers such as Eudragit or natural polymers such as Shellac.

20 Claims, No Drawings

TASTE MASKING FORMULATION FOR BITTER NATURAL COMPOUNDS

TECHNICAL FIELD OF THE INVENTION

The invention relates to taste masking formulations for bitter natural compounds, selected from extracts, fraction and pure phytochemicals produced in combination with a synthetic polymer or a natural polymer. The invention also relates to the novel process of producing the taste masking formulations.

BACKGROUND AND PRIOR ART OF THE INVENTION

Taste masking and development of palatable forms of bitter drugs and compounds have been one of the priority research areas in the field of Pharmaceuticals. With ever growing global demand for Nutraceuticals, it becomes equally challenging to develop palatable Nutraceuticals formulations as they are most commonly administered by oral route and very often through food matrix. Many of the natural extracts, fractions and pure phytochemicals are known to be very bitter and this severely limits their applications for oral formulations. Patient's acceptance and compliance are very difficult with bitter drugs and supplements, especially when they are administered in the form of solutions, suspensions, oral disintegrating, oral dissolving & chewable formulations. The difficulty in administration of these drugs further increases in the pediatric and geriatric group of patients. Various formulation techniques, process optimization and inactive taste masking ingredients were explored by many researchers to address bitter taste of drugs and supplements.

Some of the taste masking approaches include Microencapsulation, Coating, Inclusion complexes, Ion exchange, Solid dispersion, pH modification, Adsorption, Gelation, Prodrug approach, Extrusion and Coating. Among the above techniques, Microencapsulation, Inclusion Complexation, Solid dispersion and Prodrug technology are preferred approaches and they are feasible for large scale taste masking application. There are also approaches to mask the bitterness using different types of natural and synthetic hydrophilic or lipophilic Polymers (Polymethacrylates, Pthalates), flavors, sweeteners, bitterness inhibitors, effervescent agents. The type of approach changes with physicochemical properties of active, type of dosage form, bioavailability of drug.

*Bacopa monnieri*, commonly known as water hyssop, is an important herb in Ayurveda. Supplementation of *Bacopa monnieri* has been shown to improve Cognition and reduce anxiety. It is also a reliable candidate for improving Memory formation. *Bacopa monnieri* is also an antioxidant. *Bacopa monnieri* interacts with the dopamine and serotonergic systems, but its main mechanism of action involves promoting neuronal communication. It does this by enhancing the rate at which the nervous system can communicate by increasing the growth of nerve endings, also called dendrites. Bacosides/bacopasides are the main active compounds isolated from *Bacopa monnieri* and Bacoside A is a mixture of four major saponins, which include bacoside A3, bacopaside II, jujubogenin isomer of bacopasaponin C, and bacopasaponin C. The mixture has been studied in in vitro experiments and animal models for its potential neuroprotective activity.

Cationic copolymers synthesized from dimethylaminoethyl methacrylate and neutral methacrylic acid esters such as Eudragit E 100 have been employed in various taste-masking formulations. The U.S. Pat. No. 5,275,823 discloses a chewable tablet comprising a granulate of a histamine H2-receptor antagonist and optionally Eudragit E 100 and an admixture of a taste-masking extragranular water-insoluble hygroscopic excipient. While the purpose of the extragranular water-insoluble hygroscopic excipient is to reduce or eliminate the intensely bitter taste, Eudragit E 100 can be included in the granulate to provide extra taste-masking properties. Examples show a ratio of Eudragit E 100 to drug of 1 to 10.

U.S. Pat. No. 5,489,436 discloses a chewable medicament tablet comprising a medicament coated with a taste-masking amount of a polymer blend of dimethylaminoethyl methacrylate and neutral methacrylic acid esters and a polymer selected from cellulose acetate and cellulose triacetate. This coating blend is intended to achieve a balance between taste masking, dissolution and rate of bioavailability.

U.S. Pat. No. 4,708,867 discloses a mini pellet dosage form of prednisone comprising a nonpareil seed coated with a first layer of the drug and a second layer of a copolymer of dimethylaminoethyl methacrylate and methyl methacrylate.

U.S. Pat. No. 5,013,557 discloses a spray-dried spheroidal microcapsule comprising 1-70 wt % sucralphate and 30-99 wt % of a polymer soluble in gastric fluids such as maltrin. The examples illustrate 1:1 sucralfate to maltrin microcapsules, which can be incorporated in chewable products.

U.S. Pat. No. 4,760,093 discloses a taste neutral powder form of spray-dried acetaminophen which consists essentially of about 60% to 74% by weight acetaminophen and about 26% to 40% by weight of a copolymer, cationic in character, based on dimethyaminoethyl methacrylate and neutral methacrylic acid esters.

There is much less literature available on the taste masking of bitter natural extracts/fractions or pure compounds or nutraceuticals, because masking of the same is relatively complicated when compared to synthetic drugs and hence less attempts have been made.

Moreover, the techniques disclosed in the prior art for synthetic drugs have some inherent disadvantages, which include lack of stability of the formulation resulting in reappearance of the bitter taste when the formulation is subjected to physical stress, dose formulation, liquid formulation, dissolution in liquid. In addition, these techniques affect the stability and bioavailability of the actives.

Hence, the major objective of the present invention is to develop a method to prevent the bitter taste of natural extracts, fraction and pure compounds containing alkaloids, glycoside containing polyhydroxyl groups and triterpenoid saponins and sterols etc. and to provide taste masking formulations thereof.

SUMMARY OF THE INVENTION

In the major aspect, the present invention provides a method for masking of the bitter taste of extracts, fractions and pure phytochemicals derived from plant raw materials by formulating the same in combination with a cationic synthetic polymer based on dimethylaminoethyl methacrylate, butyl methacrylate, and methyl methacrylate or a natural polymer selected from different grades of chitosan, different grades of shellac etc. The ratio of bitter compound to Polymer is preferably in the range of 10:1-1:10.

In another aspect, the invention provides the process for the production of taste masking (non-bitter) formulation for bitter compounds selected from the extracts, fractions and pure phytochemicals derived from plant materials, for example, the extract of *Bacopa monnieri*.

In a further aspect, the invention provides taste masking based on the principle of hydrophobic polymer interaction between the polymer and hydrophobic portion of actives in the extract, fraction or pure compound and subsequent precipitation of the taste masked product. The precipitation and hydrophobic polymer interaction is achieved by adding an anti-solvent of high dielectric constant such as water to the drug polymer solution at a specified solvent to anti-solvent ratio.

DESCRIPTION OF THE INVENTION

Drug or active as used herein refers to phytochemical(s) in the extracts, fractions or pure compounds, which cause bitter taste.

Herbal products are becoming very popular recently as consumers are showing preference for natural and traditional medicines. Plant extracts and pure phytochemicals constitute significant part of many traditional systems of medicine, dietary supplements, botanical medicine and Nutraceuticals. Phytochemicals are natural compounds found in plants and are responsible for providing color, flavor, and aroma to fruits and vegetables. Epidemiological studies have shown that high intakes of phytochemical containing fruits and vegetables are correlated with lower risks of chronic diseases and obesity. The phytochemicals include phenols and polyphenols, alkaloids, flavonoids, isoflavones, terpenes, and glucosinolates.

However, most, if not all, of these bioactive compounds are generally comes with very poor organoleptic properties such as bitter, acrid, or astringent and therefore unpalatable to the consumer necessitating the need for masking the bitter ingredients. As a result, the food and supplement industry either routinely removes these compounds from plant foods or adopt a variety of debitterizing or taste masking processes for improving the consumer acceptance. *Bacopa monnieri* extract is one such plant product with potential nootropic applications in traditional medicine for longevity and cognitive enhancement. Its supplementation is known to reduce anxiety and improve memory function. Its efficacy is well proven by numerous human clinical trials including those in children. Unfortunately, the extracts of *Bacopa* are very bitter in taste and highly unpalatable and this has become a potential limitation for its use in medicine, food and beverage formulations.

LN17098, a natural *Bacopa monnieri* extract standardized to 55% total *bacopa* saponins by Spectrophotometric method is used for demonstrating the invention. The presence of polyhydroxyl groups is responsible for solubility of extract LN17098 in oral pH, whereas the hydrophobic portion of the extract binds to the taste receptors triggering bitter response. By understanding the chemistry of the *Bacopa* actives and physiology of taste receptors the bitter taste of LN17098 can be modified or masked by two approaches.
 1. By decreasing the solubility of the LN17098.
 2. By preventing interaction between hydrophobic portions of the active in the extract with taste receptors.

There are different taste masking approaches which are being followed from past few decades. Taste masking using different types of technologies such as Microencapsulation, Coating, Inclusion complexes, Ion exchange, Solid dispersion, pH modification, Adsorption, Gelation, Prodrug approach, Extrusion and Coating techniques are currently in use. Though each of these techniques has some unique advantages, they suffer from some inherent disadvantages. For example, 1) reappearance of bitterness when breaking of granules prepared by Granulation technique occur during the process of compression or shipping, improper coating and lack of robust film coating by Coating technique, 2) Possible cross reaction may occur between core and wall material and difficulty in achieving continuous and uniform film by Microencapsulation technique, 3) most of the polymers used in Solid dispersions technique can absorb moisture, which may result in phase separation, crystal growth or conversion from the amorphous to the crystalline state or from a metastable crystalline form to a more stable structure during storage, 4) The toxicity associated with the coating or complexing agent such as cyclodextrin (e.g., DM-β-CD) has often been a concern. 5) also there could be issues with the stability of the active in taste masking formulation during its transport across the gut.

Therefore, the present inventors have conducted research studies to develop a taste masking formulation for bitter extracts, fractions and pure compounds of plant origin without the said disadvantages. It was found surprisingly that taste masking formulation of bitter compounds with synthetic cationic polymers or a natural polymer selected from different grades of chitosan, different grades of shellac, using a novel process based on the concept of difference in dielectric constants of solvents and anti-solvents that results in the co-precipitation of taste masked product which showed unique properties and completely devoid of the inherent bitter taste.

The novel concept of the present invention is demonstrated below taking *Bacopa monnieri* extract (LN17098) as an example for bitter compound and EUDRAGIT® E 100 (a cationic copolymer based on dimethylaminoethyl methacrylate, butyl methacrylate, and methyl methacrylate) as polymer for illustration. Briefly, for effective taste masking of *Bacopa monnieri* extract (active), a cationic polymer having similar dielectric constant requirement for optimum solubility has to be selected for complexation with the actives of the extract, so that the actives in the extract and the polymer, both are freely soluble in the same organic solvent of suitable dielectric constant. In the dissolved state in ethanol, the free polymeric chains are in a state of spread out and stretched condition and at this state, some complex formation between bacopa active and the polymer occurs. This complexation between polymer and the drug molecule can be made even stronger and stable at micro and nano molecular level by co-precipitation using the concept of dielectric constant modulation. This was achieved by altering the solubility of dissolved polymer and the active in the medium through a process of dilution using an anti-solvent (manufacturing solvent) of significantly different dielectric constant, that is water in this case, and thus subjecting the polymer and active to get co-precipitated by formation of hydrophobic complex. During the process of precipitation the free polymeric chains get bended on to the surface of active molecule. Here the cohesive forces dominate the adhesive forces, which are acting between the polymeric chains. The taste masking formulation-1 obtained with *Bacopa monnieri* extract (LN17098) and EUDRAGIT® E 100 has shown very effective taste masking properties.

The said taste masking formulation of *Bacopa* extract, which addresses all the disadvantages mentioned in the existing literature, is innovative as current method uses the concept of dielectric constant for creating hydrophobic polymer interactions with the hydrophobic groups of the active compounds in the extract there by decreasing solubility of drug by blocking free hydroxyl groups in the active compounds in addition to creating a barrier between active bitter compounds and receptors of taste buds and thus achieving the taste masking.

This novel process eliminates the intensely bitter taste of natural plant extracts by simple complexation process, which occurs at micro and nano molecular level of drug molecules. Hence the quantity of free drug available at different micron size is reduced which eliminates the bitter after taste generally associated with other techniques.

This process of taste masking approach requires 2 different types of vehicles which are as follows Solvent:

Solvent is a medium used for dissolving the polymer and active during the process of taste masking and it is generally semi polar or non-polar solvent whose dielectric constant is between 04 and 40. Using this type of solvents, one can solubilize the active and polymer using a required volume of solvent. The active and polymer molecules are available in molecular state and are held together by vanderwaal forces of attraction.

Manufacturing Vehicle:

The manufacturing vehicle is a solvent/solution medium that acts as anti-solvent for causing the precipitation during the process of taste masking and it is a polar solvent having high dielectric constant in the range of 40-120 or more and it should be miscible in organic solvent. The higher the difference between the dielectric constant values of the solvent and manufacturing vehicle the greater the taste masking. The manufacturing solvent may be selected for example, from Water, 1.0-7.8 pH buffer, Methylene ketone, Ethylene glycol, Chlorinated Hydrocarbon, Aliphatic and aromatic organic solvents, Esters, 2-5% w/v Sodium chloride Even though the above technique has been demonstrated taking *Bacopa* as an example, it can be applied to other natural bitter extracts, fractions and pure compounds using a proper selection of solvent and manufacturing vehicle.

This process of taste masking eliminates the process of diffusion to occur as there is formation of strong, robust, uniform, non-flexible complexation between drug/active and polymer which further decreases the effective surface area of active compound available for sensation of bitterness. Hence free drug available at different micron sizes is reduced, which eliminates the bitter after taste generally associated with other techniques. As the entrapment of the bitter dug/active is strong at micro and nano molecular level there is no possibility of losing the taste masking effect during the process of compaction.

Accordingly, in a preferred embodiment, the invention provides a taste masked nutraceutical or dietary supplement complex which comprises;
  a) at least one bitter natural compound and
  b) a polymer, which is a synthetic polymer selected from methylated or butylated methacrylate polymers or a natural polymer selected from shellac or chitosan, where in the ratio of bitter compound to Polymer is in the range of 10:1-1:10, and wherein, the complex exhibits hydrophobic polymeric drug interactions between the hydrophobic parts of polymer and those of bitter actives.

The Adhesive forces active in the complex are hydrophobic polymeric drug interactions between the hydrophobic parts of polymer and those of bitter actives, which prevents the access/interaction of free hydroxyl groups to taste receptors and as a result blocking sensation to bitterness. In addition, the free active drug available at particle of different micron sizes are reduced which eliminates the bitter after taste generally associated with other techniques.

In this concept of taste masking approach a complex is formed between cationic group of polymer and polyhydroxy group of the active molecules in the extract, thus achieving the good taste masking by
  a. Forming strong Hydrophobic polymeric drug interaction
  b. Reducing the availability of free active molecule/hydroxyl groups available for rapid dissolution in salival pH.

It was also found surprisingly that similar taste masking effects can be achieved by using natural polymers selected from different grades of shellac and Chitosan, different grades of Shellac adopting similar approach of Dielectric constant difference by creating hydrophobic polymeric interaction during the process of precipitation. For example, shellac was dissolved in ethanol and the solution was then treated with *Bacopa monnieri* extract (LN17098). The homogenous solution was then treated with a solution of high dielectric constant such as 2% or 4% w/v of NaCl in water which resulted in rapid complexation and precipitation. The precipitate was filtered, dried under vacuum and the dry flakes were pulverized and sieved to obtain the powder formulation. A taste evaluation study has indicated very effective bitter taste masking for the formulation with higher % of NaCl. The study further confirms that increasing the dielectric constant of water by addition of strong electrolytes forms better complexation among the bitter extracts and the polymer.

The dielectric constant difference between the solvent and manufacturing solvent should be inversely proportional to each other. The optimum ratio between the solvent and the manufacturing solvent is in the range of 1:1 to 1:10 and the polymer and solvent is in the range of 1:1 to 1:10.

The aforementioned process is followed to prepare various taste masked formulations using different bitter compounds, polymers, solvents and manufacturing solvents (of various dielectric constants) at different ratios. The experimental conditions are and tabulated in tables 1-6. A taste evaluation study was conducted for all formulations 1-45. A total of 3 volunteers have participated in each taste masking evaluation study. Based on the gustatory stimuli felt by the volunteer a suitable scoring criterion is assigned as summarized in table-7 and the results obtained for different formulations are tabulated in table 8 and 9. It is evident from the taste evaluation study that the taste masking formulations disclosed in the present invention showed very significant taste masking effect.

The prepared taste masked formulations were further analyzed using validated HPLC method in order to check the affect of inventive manufacturing process on the active constituents of extracts. The details of analytical results obtained are summarized in table-10. From the analytical results it is evident that the process conditions did not interfere with the active constituents and good recovery of active constituents was observed in the formulation when compared to the input extracts used for the taste masking formulation.

Different embodiments of the present invention are as outlined below:

In the primary embodiment, the invention provides a taste masking formulation for bitter compounds comprising synthetic cationic polymer(s) or a natural polymer(s) obtained through a novel process of complexation and precipitation based on the concept of dielectric constant for selecting the solvent medium for dissolving the polymer and compound, and selecting the anti-solvent medium for dilution (manufacturing solvent) to precipitate the taste masked complex.

Accordingly, in a preferred embodiment, the invention provides a process for preparation of taste masking nutraceutical or dietary supplement formulations of bitter natural compounds comprising
 a) complexation of the bitter natural compound with a polymer in a solvent having dielectric constant in the range of 4 to 40 and
 b) co-precipitating the taste masked complex using an anti-solvent (manufacturing solvent) having dielectric constant in the range of 40 to 120.

In a detailed embodiment, the invention provides a process for producing taste masking formulations, which comprises the steps of a) preparing the polymer solution in a solvent of low dielectric constant between 04-40, under vigorous stirring; b) Preparing solution of bitter compound in polymer solution under vigorous stirring wherein the ratio between the bitter compound and polymer is in the range of 10:1 to 1:10, to obtain homogenous, translucent, viscous solution of the compound and polymer; c) diluting the said solution of polymer and bitter compound with manufacturing solvent having very high dielectric constant (40-150) such as water or salt solution under faster addition and moderate stirring to obtain a precipitate; d) separating the precipitate from the solvent by filtering; e) drying the precipitate in a vacuum dryer at 40-100° C.; f) pulverizing the flakes and sieving the powder through appropriate mesh to obtain taste masking formulation as granules of uniform size.

In one embodiment taste masking is achieved using different grades of synthetic polymers selected from Poly methyl methacrylates such as Poly(methacrylic acid-co-ethyl acrylate), Poly(methacylic acid-co-methyl methacrylate), Poly(methyl acrylate-co-methyl methacrylate-co-methacrylic acid), Poly(butyl methacrylate-co-(2-demethylaminoeethyl) methacrylate-co-methyl methacrylate), Poly(ethyl acrylate-co-methyl methacrylate-co-trimethylammonioethyl methacrylate chloride), Poly (butyl methacrylate-co-(2-dimethylaminoethyl)methacrylate-comethyl methacrylate), Poly (methyl acrylate-co-methylmethacrylate-co-methacrylic acid), Poly (ethylacrylate-co-methyl methacrylate) which shows different type of drug release, site specific drug delivery, to maintain stability of drug and to avoid side effects associated with particular type of site specific delivery, to obtain non-tacky and easily processed films on the surface of drug molecule.

In other key embodiment, taste masking is achieved using different grades of marketed Eudragit polymers selected from Eudragit E 100, Eudragit L 100, Eudragit L30D-55, Eudragit L 100-55, Eudragit L 12.5, Eudragit S 100, Eudragit S 12.5, Eudragit FS 30D, Eudragit E 12.5, Eudragit E PO, Eudragit RL 100, Eudragit RL PO, Eudragit RL 30D, Eudragit RL 12.5 and also Kollicoat grade of similar polymers.

In the other embodiment, the natural polymer is selected from different grades of chitosan such as shrimp shell chitosan, deacylated chitosan different grades of shellac such as Dewaxed bleached shellac, Dewaxed Decolorized shellac, etc.)

In other embodiment, taste masking is achieved based on hydrophobic polymer interaction between hydrophobic portions of the polymer and hydrophobic portion of natural active (drug) by selecting a high dielectric constant difference between the solvent selected for drug and polymer solution and that used for dilution, wherein dielectric constant for the solvent used for preparation of drug/polymer solution is low and that of the solvent used for dilution is of high dielectric constant or vice versa.

In other embodiment, the solvent used for dissolving polymer can be ethanol, methanol, isopropyl alcohol and ethyl acetate, water, Acetone, Butanol, Methylene chloride, 1N Hydrochloric acid, Butyl glycerol and Benzyl alcohol etc. The solvent used for preparing polymeric solution is based on selection of polymer for desired site of action. The type of solvent used for preparing polymer- and bitter compound solution is based on solubility of the polymer in that particular solvent.

In another embodiment, invention provides compositions containing said taste masking formulation optionally containing at least one inert ingredient/excipient/carrier(s) selected from disintegrants, Glidants, lubricants, diluents, or preservatives.

In other embodiment, the invention provides dosage forms containing the above taste masking formulations, wherein the dosage forms include different types of tablets (oro dispersible tablets, chewable tablets, effervescent and non-effervescent tablets, sublingual tablets, buccal tablets and also site specific drug delivery tablet) and capsules, liquid dosage forms (such as suspensions, solutions, beverages), semisolid, food and confectionary, milk products, etc. . . . In other embodiment, the percentage of polymer in the polymer-drug solution can vary in the range of 10-80%. The % of solvent is selected based on required viscosity of drug-polymer solution.

In another embodiment, the ratio between the bitter extracts/fractions/compounds and the polymer in the taste masking formulation varies in the range of 1:0.1 to 1:10, and the ratio between the solvent used for dissolving the polymer and the extract/fraction/compound and the solvent used for precipitation (manufacturing vehicle) varies in the range from 1:0.1 to 1:100.

In other embodiment, the drug polymeric complex can be precipitated in the process for the preparation of the taste masking formulation by adding solvent or solution of high dielectric constant.

In other embodiment, the taste masking formulation for bitter compounds, wherein the bitter compounds are different plant derivatives selected from extracts, fractions or compounds containing glycoside and their derivatives, terpenes, sterols or steroids, saponins, alkaloids, tannins, polyphenols, proanthocyanidins, flavonoid and other category of extracts.

In other embodiment, the taste masking formulation for bitter compounds, wherein the bitter compounds are different plant derivatives selected from extracts, fractions or compounds containing *Bacopa monnieri, Azadirachta indica, Momordica charantia, Picrorhiza kurroa, Mangifera indica, Garcinia mangostana, Boswellia serrata, Withania somnifera*, and *Andrographis paniculata*, and other category of bitter compounds. In one embodiment, the bitter natural compound is an extract of *Bacopa monnieri* standardized to 20-70% total bacosides by UV spectrometric method of analysis and/or 5-25% total bacosides (bacoside A3, Bacopaside I, bacopaside II, jujubogenin isomer of bacopasaponin C, and bacopasaponin C) by HPLC method of analysis.

In other embodiment, the current taste masking formulations can be used for making dosage forms, which include tablets of different type such as Enteric coated granules or tablets (if the type of polymethacrylate polymer used is of enteric type), chewable formulations, gummy snacks colon targeted granules (if the type of polymethacrylate polymer used is of colon targeted), pH dependent drug release based on site specific delivery of Liquid orals (such as suspensions, solutions, beverages of different types) using polymethacrylates which show site specific polymers of polymethacrylate polymers.

In one embodiment, the dose of final formulation is based on type of dosage form (solid dosage forms. liquid dosage forms, food products, beverages, confectionaries) and age group and different races of population, wherein the general solid dosage form varies in the range between 25-1000 mg in single or divided doses.

This technique of taste masking reduces the interaction of hydrophobic active molecule with the receptors of the taste buds, along with reducing the access of free hydroxyl groups available for rapid dissolution in saliva pH. These types of reducing/preventing hydrophobic interaction with taste receptors itself reduce the intensity of bitterness of bitter compounds.

The following examples, which include preferred embodiments, will serve to illustrate the practice of this invention, and it being understood that the particulars shown are by way of example and for purpose of illustrative discussion of preferred embodiments of the invention and they are not to limit the scope of the invention.

EXAMPLE 1 a) Preparation of *Bacopa monnieri* Extracts LN17096D, LN17097, LN17098, LN17096E, LN17096B, LN17096A, and LN17096C.

Dried plant material of *Bacopa monnieri* (1 Kg) was pulverized to coarse powder, extracted with 80% aqueous alcohol three times (8+5+5) for 2 hrs at reflux temp.

The combined extracts were fine filtered and concentrated to dryness under reduced pressure to give powder residue (LN17096D; 225-240 g) containing 25% total bacopasides UV spectrophotometric method and 5-8% total bacosides (bacoside A3, Bacopaside I, bacopaside II, jujubogenin isomer of bacopasaponin C, and bacopasaponin C) by HPLC method of analysis.

To the crude alcoholic extract (100 g) obtained above was added water (200 mL) and the mixture was kept under stirring for 30 min. The insoluble powder was filtered to obtain the solid compound. The procedure was repeated once again and the solid obtained was subjected to drying in a vacuum dryer at 75-80° C. temperature. The solid was pulverized and sieved through 60 mesh to obtain a powder extract (LN17097). It showed 60% total bacopasides by UV method of analysis and 20% total bacosides (bacoside A3, Bacopaside I, bacopaside II, jujubogenin isomer of bacopasaponin C, and bacopasaponin C) by HPLC method of analysis.

LN17098 is a commercial grade of *Bacopa monnieri* extract currently being marketed by Soho Flordis International (SFI), Sydney, Australia under the trade name Keenmind and also being marketed by PLT Health Solutions Inc, N.J., USA under the trade name Synapsa. A sample of LN17098 is obtained from Laila Nutraceuticals, Vijayawada, India. It is standardized to greater than 55% total bacopasides by UV spectrometric method of analysis and 8-15% total bacosides (bacoside A3, Bacopaside I, bacopaside II, jujubogenin isomer of bacopasaponin C, and bacopasaponin C) by HPLC method of analysis.

The dried plant material *Bacopa monnieri* (100 g) was pulverized to coarse powder, extracted with 80% methanol three times (5+3+3 L) for 1.5-2 h each time at reflux temperature. The extracts were combined, fine filtered and concentrated to dryness under reduced pressure to give a residue (10 g; LN17096E)

The dried plant material of *Bacopa monnieri* (100 g) was pulverized to coarse powder, extracted with methanol (5 L) 1.5 to 2 hours at reflux temperature. The extract was filtered and residue extracted two more times with 3 L of methanol each time under similar conditions. The extracts were combined, fine filtered and concentrated to dryness under reduced pressure to give residue 17 g (LN17096B).

The dried plant material of *Bacopa monnieri* (100 g) was pulverized to coarse powder, extracted with ethanol (5 L) 1.5 to 2 hours at reflux temperature. The extract was filtered and residue extracted two more times with 3 L of ethanol each time under similar conditions. The extracts were combined, fine filtered and concentrated to dryness under reduced pressure to give residue 16 g (LN17096A).

Dried plant material *Bacopa monnieri* (1 Kg) was pulverized to coarse powder, extracted with water three times (8+5+5) for 2 hrs at room temp. The combined extracts were fine filtered and concentrated to dryness under reduced pressure to give water extract of *Bacopa monnieri* (105 g; LN17096C).

b) Preparation of Ashwagandha Extract (LN17100)

Dried plant material of Ashwagandha (100 g) was pulverized to coarse powder, extracted with methanol three times (4+3+3) for 1½-2 hrs at reflux temp. The combined extracts were fine filtered and concentrated to dryness under reduced pressure to give residue 12-14 g LN17100 c) Preparation of Neem Extract (LN17099)

Dried plant material of Neem (*Azadirachta indica*) leaves (100 g) was pulverized to coarse powder, extracted with methanol three times (5+3+3) for 1½-2 hrs at reflux temp. The combined extracts were fine filtered and concentrated to dryness under reduced pressure to give residue 12-14 g LN17099.

d) Preparation of Karela Extracts (LN17101)

Dried plant material Karela (*Momordica charantia*) fruit (100 g) was pulverized to coarse powder, extracted with methanol three times sequentially with 5, 3, 3 L for 1.5-2 hrs at reflux temp. The combined extracts were fine filtered and concentrated to dryness under reduced pressure to give residue 10-12 g, LN17101.

EXAMPLE 2

Process for Taste Masking of LN17098 with Eudragit E 100 Formulation-1

Step-1: Preparation of Eudragit E 100 Ethanolic Solution

Measure accurately 100 mL of ethanol and transfer the content in to a clean and dry round bottom flask (RBF). Weigh 10 g of polymer (Eudragit E 100) and transfer the contents slowly to the above ethanolic solution under constant stirring. Allow the contents to mix well until homogenous, clear solution is obtained.

Step-2: Preparation LN17098-Eudragit E 100 Solution

To the above prepared polymeric solution, 100 g of LN17098 extract was added slowly under constant stirring. After complete addition, the contents were mixed for about 20-30 minutes to obtain homogenous LN17098-Polymer solution.

Step-3: Precipitation of LN17098-Eudragit E 100 Complex

To the above prepared LN17098-Polymeric solution add 600 mL of water and allows the contents to stir under low rpm (<100) until the complex is precipitated completely.

Step-4: Filtration, Drying, Pulverization and Sieving

Filter the obtained complex through suitable filter's and dry the filtrate using suitable vacuum dryer at 50-60° C. After complete drying collect the obtained flakes of LN17098-Polymeric complex and pulverize using suitable multi mill by employing required mesh. The pulverized powder is passed through suitable sieve.

The aforementioned process is followed to prepare various taste masked formulations using different bitter compounds, polymers, solvents and manufacturing solvents (of various dielectric constants) with different ratios and different temperatures (40-100° C.) tabulated in table 1-6.

TABLE 1

Taste masked formulations of LN17098 with Eudragit E100

| S. NO | Formulation# | LN17098 (Active) (gm) | Eudragit E100 (polymer) (gm) | Ethanol (Solvent) (mL) | Water (Anti-solvent) (mL) | Active to polymer Ratio | Solvent to anti-solvent Ratio | Polymer to Solvent ratio |
|---|---|---|---|---|---|---|---|---|
| 1 | Formulation-1 | 100 | 10 | 100 | 600 | 10:1 | 1:6 | 1:10 |
| 2 | Formulation-2 | 66.66 | 33.33 | 330 | 1980 | 2:1 | 1:6 | 1:10 |
| 3 | Formulation-3 | 57.14 | 42.86 | 428.6 | 2571 | 1:0.75 | 1:6 | 1:10 |
| 4 | Formulation-4 | 33.33 | 66.66 | 666.66 | 3999.96 | 1:2 | 1:6 | 1:10 |
| 5 | Formulation-5 | 20 | 80 | 800 | 4800 | 1:4 | 1:6 | 1:10 |
| 6 | Formulation-6 | 10 | 100 | 1000 | 6000 | 1:10 | 1:6 | 1:10 |
| 7 | Formulation-7 | 66.66 | 33.33 | 33 | 198 | 2:1 | 1:6 | 1:1 |
| 8 | Formulation-8 | 66.66 | 33.33 | 330 | 330 | 2:1 | 1:1 | 1:10 |
| 9 | Formulation-9 | 66.66 | 33.33 | 330 | 3300 | 2:1 | 1:10 | 1:10 |

TABLE 2

Taste masked formulations of LN17098 with different solvents

| S. NO | Formulation# | LN17098 (gm) | Eudragit E 100 | Solvent | Dielectric constant | Solvent quantity (ml) | Water (ml) |
|---|---|---|---|---|---|---|---|
| 1 | Formulation-10 | 66.66 g | 33.33 g | Methanol | 33 | 233.31 | 1399 |
| 2 | Formulation-11 | 66.66 g | 33.33 g | Isopropyl alcohol | 17.5 | 330 | 1980 |
| 3 | Formulation-12 | 66.66 g | 33.33 g | Acetone | 21.5 | 330 | 1980 |
| 4 | Formulation-13 | 66.66 g | 33.33 g | Ethyl acetate | 6 | 330 | 1980 |

TABLE 3

Taste masked formulations of various bitter compounds with Eudragit E100

| S. NO | Formulation# | Bitter compound | Bitter compound quantity (grams) | Eudragit E 100 (grams) | Ethanol (ml) | Water quantity (ml) |
|---|---|---|---|---|---|---|
| 1 | Formulation-14 | LN17096A | 66.66 | 33.33 | 330 | 1980 |
| 2 | Formulation-15 | LN17096B | 66.66 | 33.33 | 330 | 1980 |
| 3 | Formulation-16 | LN17096D | 66.66 | 33.33 | 330 | 1980 |
| 4 | Formulation-17 | LN17096C | 66.66 | 33.33 | 330 | 1980 |
| 5 | Formulation-18 | LN17097 | 66.66 | 33.33 | 330 | 1980 |
| 6 | Formulation-19 | LN17096E | 66.66 | 33.33 | 330 | 1980 |
| 7 | Formulation-20 | LN17099 | 66.66 | 33.33 | 330 | 1980 |
| 8 | Formulation-21 | LN17100 | 66.66 | 33.33 | 330 | 1980 |
| 9 | Formulation-22 | LN17101 | 66.66 | 33.33 | 330 | 1980 |

TABLE 4

Taste masked formulations of LN17098 with shellac

| S. NO | Formulation# | LN17098 (Active) (gm) | Shellac (polymer) (gm) | Ethanol (Solvent) (mL) | 4% w/v NaCl (Anti-solvent) (mL) | Active to polymer Ratio | Solvent to anti-Solvent Ratio | Polymer to Solvent ratio |
|---|---|---|---|---|---|---|---|---|
| 1 | Formulation-23 | 100 | 10 | 220 | 1100 | 10:1 | 1:5 | 1:22 |
| 2 | Formulation-24 | 66.66 | 33.33 | 200 | 1000 | 2:1 | 1:5 | 1:6 |
| 3 | Formulation-25 | 57.14 | 42.86 | 200 | 1000 | 1:0.75 | 1:5 | 1:4 |
| 4 | Formulation-26 | 33.33 | 66.66 | 200 | 1000 | 1:2 | 1:5 | 1:3 |
| 5 | Formulation-27 | 20 | 80 | 200 | 1000 | 1:4 | 1:5 | 1:2.5 |
| 6 | Formulation-28 | 10 | 100 | 220 | 1100 | 1:10 | 1:5 | 1:2.2 |
| 7 | Formulation-29 | 50 | 50 | 50 | 500 | 1:1 | 1:10 | 1:1 |
| 8 | Formulation-30 | 50 | 50 | 500 | 500 | 1:1 | 1:1 | 1:10 |

TABLE 5

Taste masked formulations of LN17098 with shellac and different solvents

| S. NO | Formulation# | LN17098 (g) | Shellac (g) | Solvent | Solvent quantity (mL) | 4% w/v NaCl (ml) |
|---|---|---|---|---|---|---|
| 1 | Formulation-31 | 50 | 50 | Methanol | 350 | 1750 |
| 2 | Formulation-32 | 50 | 50 | Isopropyl alcohol | 250 | 3500 |
| 3 | Formulation-33 | 50 | 50 | Acetone | 250 | 3500 |
| 4 | Formulation-34 | 50 | 50 | Ethyl acetate | 500 | 3500 |

TABLE 6

Taste masked formulations of various bitter compounds with shellac

| S. NO | Formulation | Bitter compound | Bitter compound quantity (g) | Eudragit E 100 (g) | Ethanol (ml) | 4% w/v NaCl (ml) |
|---|---|---|---|---|---|---|
| 1 | Formulation-35 | LN17096A | 50 | 50 | 200 | 1000 |
| 2 | Formulation-36 | LN17096B | 50 | 50 | 200 | 1000 |
| 3 | Formulation-37 | LN17096D | 50 | 50 | 200 | 1000 |
| 4 | Formulation-38 | LN17096C | 50 | 50 | 200 | 1000 |
| 5 | Formulation-39 | LN17097 | 50 | 50 | 200 | 1000 |
| 6 | Formulation-40 | LN17096E | 50 | 50 | 200 | 1000 |
| 7 | Formulation-41 | LN17099 | 50 | 50 | 200 | 1000 |
| 8 | Formulation-42 | LN17100 | 50 | 50 | 200 | 1000 |
| 9 | Formulation-43 | LN17101 | 50 | 50 | 200 | 1000 |

EXAMPLE-3

Taste Evaluation Report

A taste evaluation study was conducted for all formulations 1-45. A total of 3 volunteers have participated in the study. Based on the gustatory stimuli felt by the volunteer a suitable scoring is given as per table-7.

TABLE 7

Scoring for various Gustatory Stimuli

| S. NO | Gustatory Stimuli | Score |
|---|---|---|
| 1 | Intensely Bitter | 5 |
| 2 | Bitter | 4 |
| 3 | Moderately Bitter | 3 |
| 4 | Slightly Bitter | 2 |
| 5 | No Taste | 1 |

TABLE 8

Taste evaluation report of formulations 1-23

| S. NO | Formulation# | Volunteer-1 | Volunteer-2 | Volunteer-3 |
|---|---|---|---|---|
| 1 | Formulation-1 | 2 | 3 | 2 |
| 2 | Formulation-2 | 2 | 3 | 3 |
| 3 | Formulation-3 | 1 | 1 | 1 |

TABLE 8-continued

Taste evaluation report of formulations 1-23

| S. NO | Formulation# | Volunteer-1 | Volunteer-2 | Volunteer-3 |
|---|---|---|---|---|
| 4 | Formulation-4 | 1 | 1 | 1 |
| 5 | Formulation-5 | 1 | 1 | 1 |
| 6 | Formulation-6 | 1 | 1 | 1 |
| 7 | Formulation-7 | 1 | 1 | 2 |
| 8 | Formulation-8 | 2 | 3 | 3 |
| 9 | Formulation-9 | 1 | 1 | 1 |
| 10 | Formulation-10 | 1 | 2 | 1 |
| 11 | Formulation-11 | 1 | 1 | 2 |
| 12 | Formulation-12 | 1 | 1 | 2 |
| 13 | Formulation-13 | 1 | 1 | 2 |
| 14 | Formulation-14 | 1 | 2 | 1 |
| 15 | Formulation-15 | 1 | 1 | 2 |
| 16 | Formulation-16 | 1 | 1 | 1 |
| 17 | Formulation-17 | 1 | 1 | 1 |
| 18 | Formulation-18 | 1 | 1 | 1 |
| 19 | Formulation-19 | 1 | 1 | 1 |
| 20 | Formulation-20 | 2 | 3 | 2 |
| 21 | Formulation-21 | 1 | 1 | 1 |
| 22 | Formulation-22 | 1 | 1 | 1 |

TABLE 9

Taste evaluation report of formulations 24-45

| S. NO | Formulation# | Volunteer-1 | Volunteer-2 | Volunteer-3 |
|---|---|---|---|---|
| 1 | Formulation-23 | 3 | 2 | 2 |
| 2 | Formulation-24 | 2 | 2 | 2 |
| 3 | Formulation-25 | 2 | 2 | 2 |
| 4 | Formulation-26 | 2 | 2 | 3 |
| 5 | Formulation-27 | 1 | 1 | 1 |
| 6 | Formulation-28 | 1 | 1 | 1 |
| 7 | Formulation-29 | 2 | 1 | 1 |
| 8 | Formulation-30 | 1 | 2 | 1 |
| 9 | Formulation-31 | 2 | 2 | 1 |
| 10 | Formulation-32 | 1 | 1 | 1 |
| 11 | Formulation-33 | 2 | 2 | 1 |
| 12 | Formulation-34 | 1 | 2 | 1 |
| 13 | Formulation-35 | 1 | 1 | 2 |
| 14 | Formulation-36 | 1 | 1 | 1 |
| 15 | Formulation-37 | 2 | 2 | 2 |
| 16 | Formulation-38 | 3 | 2 | 1 |
| 17 | Formulation-39 | 2 | 2 | 2 |
| 18 | Formulation-40 | 1 | 1 | 1 |
| 19 | Formulation-41 | 2 | 3 | 2 |
| 20 | Formulation-42 | 1 | 1 | 1 |
| 21 | Formulation-43 | 2 | 2 | 2 |

EXAMPLE-4

Analytical Studies

The prepared taste masked formulations were further analyzed using validated HPLC method in order to check the effect of process on active constituents of extracts. The analytical studies were carried out for pure actives as well as formulations. Based on the formulation various % assay was recovered. When compared to pure active the formulation % assay is less which is due to addition of taste masking polymer to the formulation. The expected % assay values listed in Table 10 are theoretical assay that is estimated based on composition of bitter compound: polymer. The details of analytical results obtained are given in table-10. From the table it can be observed that the % assay values of formulation correlates with theoretical calculated values.

TABLE 10

Analytical data

| | | % Assay of Total Bacosides | | |
|---|---|---|---|---|
| S. NO | Formulation | Pure Extract | Theoretically Expected % of Bacosides | Taste Masked Formulation |
| 1 | Formulation-2 | 21.62 | 14.41 | 11.77 |
| 2 | Formulation-16 | 6.22 | 4.14 | 5.07 |
| 3 | Formulation-17 | 10.2 | 6.8 | 7.59 |
| 4 | Formulation-19 | 9.85 | 6.54 | 6.36 |
| 5 | Formulation-38 | 6.22 | 3.11 | 2.44 |
| 6 | Formulation-39 | 10.2 | 5.1 | 4.28 |
| 7 | Formulation-41 | 9.85 | 4.92 | 3.88 |
| 8 | Formulation-42 | 6.38 | 3.19 | 2.39 |

From the analytical results it is evident that the method does not interfere with active constituents and sufficient assay was observed in the formulation.

We claim:

1. A taste masked nutraceutical or dietary supplement formulation comprising a complex between at least one bitter natural compound and a polymer, wherein the polymer is a synthetic polymer or a natural polymer;
    wherein the synthetic polymer is selected from the group consisting of:
        a copolymer consisting of an unsubstituted Cl to C4 alkyl ester of acrylic acid, methacrylic acid, or a mixture thereof; and methacrylic acid; and
        a cationic copolymer of an unsubstituted Cl to C4 alkyl ester of acrylic acid, methacrylic acid, or a mixture thereof; and a cationic methacrylic ester;
    wherein the natural polymer is shellac; and
    wherein:
        the ratio of the bitter natural compound to the polymer ranges from 10:1 to 1:10;
        the complex exhibits hydrophobic polymeric drug interactions between a hydrophobic part of the polymer and the bitter natural compound; and
        the formulation does not include both a synthetic polymer and a natural polymer.

2. The taste masked nutraceutical or dietary supplement formulation as claimed in claim 1, wherein the bitter natural compound is an extract of a plant part, said plant part being obtained from a plant selected from the group consisting of *Bacopa monnieri, Azadirachta indica, Momordica charantia, Picrorhiza kurroa, Mangifera indica, Garcinia mangostana, Boswellia serrata, Withania somnifera*, and *Andrographis paniculata*.

3. The taste masked nutraceutical or dietary supplement formulation as claimed in claim 1, wherein the taste masked formulation further comprises at least one additional ingredient selected from the group consisting of flavoring agents, sweeteners, effervescent materials, and diluents or carriers;
    wherein the at least one additional ingredient is suitable for making chewable tablets, orodispersible tablets, dry syrups, dry powders for suspension, suspensions, disintegrating tablets, fast dissolving tablets, or sachets.

4. The taste masked nutraceutical or dietary supplement complex as claimed in claim 1, wherein the bitter natural compound is an extract of *Bacopa monnieri*.

5. The taste masked nutraceutical or dietary supplement formulation as claimed in claim 4, wherein the bitter natural compound is an extract of *Bacopa monnieri* standardised to 20-70% total bacosides by UV spectrometric method of analysis and/or 5-25% total bacosides by HPLC method of analysis.

6. The taste masked nutraceutical or dietary supplement formulation as claimed in claim 4, wherein the bitter natural compound is an extract of *Bacopa monnieri*, said extract of *Bacopa monnieri* comprising the bacosides bacoside A3, Bacopaside I, bacopaside II, jujubogenin isomer of bacopasaponin C, and bacopasaponin C.

7. A taste masked nutraceutical or dietary supplement formulation comprising at least one bitter natural compound and a polymer, wherein:
    the ratio of the bitter natural compound to the polymer ranges from 10:1 to 1:10;
    the polymer is a cationic synthetic copolymer of a Cl to C4 alkyl ester of acrylic acid, methacrylic acid, or a mixture thereof; and an aminoalkyl methacrylic ester;
    the at least one bitter natural compound has hydroxy groups; and
    a bitter natural compound-polymer complex is formed between the cationic synthetic copolymer and the hydroxy groups on the at least one bitter natural compound.

8. A process for preparation of the taste masked nutraceutical or dietary supplement formulation as claimed in claim 7, comprising
    a) complexation of the bitter natural compound with the cationic synthetic copolymer in a solvent having a dielectric constant in the range of 4 to 40, and
    b) co-precipitating the bitter natural compound-polymer complex using an anti-solvent having a dielectric constant in the range of 40 to 120.

9. The process for preparation of the taste masked nutraceutical or dietary supplement formulation as claimed in claim 4, wherein said complexation comprises:
    Preparing a solution of the cationic synthetic copolymer in the solvent having a dielectric constant in the range of 4 to 40 under vigorous stirring; and
    Preparing a solution of the bitter natural compound in the solution of the cationic synthetic copolymer under vigorous stirring, wherein the ratio of the bitter natural compound to the polymer ranges from 10:1 to 1:10.

10. The process for the preparation of the taste masked nutraceutical or dietary supplement formulation as claimed in claim 5, wherein the polymer is selected from the group consisting of Poly(butyl methacrylate-co-(2-demethylaminoethyl) methacrylate-co-methyl methacrylate), Poly(ethyl acrylate-co-methyl methacrylate-co-trimethylammonioethyl methacrylate chloride) and Poly(butyl methacrylate-co-(2-dimethylaminoethyl)methacrylate-co-methyl methacrylate).

11. The process for the preparation of the taste masked nutraceutical or dietary supplement formulation as claimed in claim 5, wherein the solvent having a dielectric constant in the range of 4 to 40 is selected from the group consisting of Ethanol, Methanol, Isopropyl alcohol, Ethyl acetate, Acetone, Butanol, Methylene chloride, 1N Hydrochloric acid, Butyl glycerol and Benzyl alcohol.

12. The process for the preparation of the taste masked nutraceutical or dietary supplement formulation as claimed in claim 4, wherein the bitter natural compound is selected from the group consisting of extracts of *Bacopa monnieri*, *Azadirachta indica*, *Momordica charantia*, *Picrorhiza kurroa*, *Mangifera indica*, *Garcinia mangostana*, *Boswellia serrata*, *Withania somnifera*, *Andrographis paniculate*, and mixtures thereof.

13. The process for preparation of taste masking nutraceutical or dietary supplement formulations of bitter natural compounds as claimed in claim 4, wherein said co-precipitating comprises:
    co-precipitating the polymer and the bitter compound by addition of an anti-solvent having a dielectric constant in the range of 40 to 120 to the solution of polymer and bitter compound.

14. The process for preparation of taste masking nutraceutical or dietary supplement formulations of bitter natural compounds as claimed in claim 4, further comprising:
    separating a bitter compound-polymer complex from the solution of polymer and bitter compound by filtration; and
    drying and pulverizing the bitter compound-polymer complex, followed by sieving the pulverized complex through an appropriate mesh to obtain the taste masked nutraceutical or dietary supplement formulation.

15. The process for the preparation of the taste masked nutraceutical or dietary supplement formulation as claimed in claim 14, wherein the ratio between the solvent and the anti-solvent is in the range of 1: 1 to 1: 10.

16. The process for the preparation of the taste masked nutraceutical or dietary supplement formulation as claimed in claim 14, wherein the anti-solvent having a dielectric constant in the range of 40 to 120 is selected from the group consisting of Water, 1.0-7.8 pH buffer, Methylene ketone, Ethylene glycol, Chlorinated Hydrocarbon, Aliphatic and aromatic organic solvents, Esters, and 2-5% w/v Sodium chloride.

17. A dosage form comprising a taste masked nutraceutical or dietary supplement formulation comprising at least one bitter natural compound and a polymer,
    wherein the polymer is a synthetic polymer or a natural polymer;
    wherein the synthetic polymer is selected from the group consisting of:
        a copolymer consisting of an unsubstituted Cl to C4 alkyl ester of acrylic acid, methacrylic acid, or a mixture thereof; and methacrylic acid; and
        a cationic copolymer of an unsubstituted Cl to C4 alkyl ester of acrylic acid, methacrylic acid, or a mixture thereof; and a cationic methacrylic ester;
    wherein the natural polymer is selected from the group consisting of:
        shellac, chitosan, and a mixture thereof;
    wherein the ratio of the bitter natural compound to the polymer ranges from 10:1 to 1:10; and
    wherein the dosage form is a tablet, a capsule, or a dry syrup.

18. The dosage form as claimed in claim 17, wherein the dosage form is a tablet selected from the group consisting of an orodispersible tablet, a chewable tablet, an effervescent tablet, a non-effervescent tablet, a sublingual tablet, and a buccal tablet.

19. The dosage form as claimed in claim 17, wherein the polymer is shellac, and the ratio of the bitter natural compound to the shellac ranges from 1:1 to 1:10.

20. The dosage form as claimed in claim 17, wherein the dosage form is a tablet or a capsule.

* * * * *